US006486373B1

(12) United States Patent
Abichandani et al.

(10) Patent No.: US 6,486,373 B1
(45) Date of Patent: **\*Nov. 26, 2002**

(54) SHAPE SELECTIVE ZEOLITE CATALYST AND ITS USE IN AROMATIC COMPOUND CONVERSION

(75) Inventors: Jeevan S. Abichandani, Voorhees, NJ (US); Daria N. Lissy, Glen Mills, PA (US); Mae K. Rubin, Bala Cynwyd, PA (US); Sanjay B. Sharma, Burr Ridge, IL (US); David S. Shihabi, Pennington, NJ (US)

(73) Assignee: Mobil Oil Corporation, Fairfax, VA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/011,171

(22) PCT Filed: Nov. 5, 1996

(86) PCT No.: PCT/US96/17720

§ 371 (c)(1),
(2), (4) Date: Nov. 4, 1998

(87) PCT Pub. No.: WO97/46636

PCT Pub. Date: Dec. 11, 1997

(51) Int. Cl.$^7$ ................................................. B01J 29/40
(52) U.S. Cl. ......................... 585/475; 585/481; 502/60; 502/64; 502/63; 502/71; 502/77; 502/85
(58) Field of Search ................................. 585/470, 475, 585/477, 481; 502/60, 64, 63, 77, 85, 71

(56) References Cited

U.S. PATENT DOCUMENTS

| | | | |
|---|---|---|---|
| 3,354,078 A | 11/1967 | Miale et al. | 208/120 |
| 3,698,157 A | 10/1972 | Allen et al. | 55/75 |
| 4,060,568 A | 11/1977 | Rodewald | 260/668 |
| 4,090,981 A | 5/1978 | Rodewald | 252/455 Z |
| 4,100,215 A | 7/1978 | Chen | 260/671 |
| 4,117,026 A | 9/1978 | Haag et al. | 260/671 R |
| 4,127,616 A | 11/1978 | Rodewald | 260/671 R |
| 4,145,315 A | 3/1979 | Rodewald | 252/455 Z |
| 4,276,437 A | 6/1981 | Chu | 585/467 |
| 4,278,827 A | 7/1981 | Chu et al. | 585/467 |
| 4,288,647 A | 9/1981 | Chu | 585/467 |
| 4,302,620 A | 11/1981 | Chu | 585/467 |
| 4,379,761 A | 4/1983 | Olson et al. | 252/435 |
| 4,465,886 A | 8/1984 | Rodewald | 585/467 |
| 4,477,583 A | 10/1984 | Rodewald | 502/71 |
| 4,927,979 A | 5/1990 | Yamagishi et al. | 568/791 |
| 4,950,835 A | 8/1990 | Wang et al. | 585/467 |
| 5,173,461 A | 12/1992 | Absil et al. | 502/62 |
| 5,365,003 A | 11/1994 | Chang et al. | 585/470 |
| 5,403,800 A | 4/1995 | Beck et al. | 502/64 |
| 5,476,823 A | 12/1995 | Beck et al. | 502/60 |
| 5,498,814 A | 3/1996 | Chang et al. | 585/475 |

Primary Examiner—Stanley S. Silverman
Assistant Examiner—Christina Ildebrando
(74) Attorney, Agent, or Firm—Ronald D. Hantman

(57) ABSTRACT

A shape-selective catalyst comprises a synthetic porous crystalline material having the structure of ZSM-5 and a composition involving the molar relationship: $X_2O_3$:(n) $YO_2$, wherein X is a trivalent element, such as aluminum, boron, iron and/or gallium, preferably aluminum; Y is a tetravalent element such as silicon and/or germanium, preferably silicon; and n is greater than about 12, and wherein the crystals have a major dimension of at least about 0.5 micron and a surface $YO_2/X_2O_3$ ratio which is no more than 20% less than the bulk $YO_2/X_2O_3$ ratio of the crystal. The crystals have a diffusion-modifying surface coating of a refractory material such as silica or coke. The catalyst is useful in a wide variety of selective hydrocarbon conversion processes, particularly the selective disproportionation of toluene to para-xylene.

17 Claims, No Drawings

SHAPE SELECTIVE ZEOLITE CATALYST AND ITS USE IN AROMATIC COMPOUND CONVERSION

This invention relates to a shape selective zeolite catalyst and its use in the conversion of aromatic compounds, particularly the selective production of para-dialkylaromatic compounds.

The term "shape-selective describes unexpected catalytic selectivities in zeolites. The principles behind shape selective catalysis have been reviewed extensively, e.g., by N. Y. Chen, W. E. Garwood and F. G. Dwyer, "Shape Selective Catalysis in Industrial Applications," 36, Marcel Dekker, Inc. (1989). Within a zeolite pore, hydrocarbon conversion reactions such as isomerization, disproportionation, alkylation and transalkylation of aromatics are governed by constraints imposed by the channel size. Reactant selectivity occurs when a fraction of the feedstock is too large to enter the zeolite pores to react; while product selectivity occurs when some of the products cannot leave the zeolite channels. Product distributions can also be altered by transition state selectivity in which certain reactions cannot occur because the reaction transition state is too large to form within the zeolite pores or cages. Another type of selectivity results from configurational constraints on diffusion where the dimensions of the molecule approach that of the zeolite pore system. A small change in the dimensions of the molecule or the zeolite pore can result in large diffusion changes leading to different product distributions. This type of shape selective catalysis is demonstrated, for example, in selective alkyl-substituted benzene dispro-portionation to para-dialkyl-substituted benzene.

A representative para-dialkyl-substituted benzene is para-xylene, which is a valuable chemical feedstock for the production of polyesters. The production of para-xylene is typically performed by methylation of toluene or by toluene disproportionation over a catalyst under conversion conditions. Examples include the reaction of toluene with methanol, as described by Chen et al., J. Amer. Chem. Soc. 101, 6783 (1979), and toluene disproportionation, as described by Pines in "The Chemistry of Catalytic Hydrocarbon Conversions", Academic Press, N.Y., 1981, p. 72. Such methods typically result in the production of a mixture of the three xylene isomers, i.e., para-xylene, ortho-xylene, and meta-xylene. Depending upon the degree of selectivity of the catalyst for para-xylene (para-selectivity) and the reaction conditions, different percentages of para-xylene are obtained. The yield, i.e., the amount of xylene produced as a proportion of the feedstock, is also affected by the catalyst and the reaction conditions.

Another well known method for producing para-xylene is by isomerization of a $C_8$ aromatic feedstock containing a high proportion of other xylene isomers, particularly meta-xylene. Commercially available $C_8$ aromatic feedstocks normally contain significant amounts of ethylbenzene, which is difficult to separate by physical methods, and hence an important object of most xylene isomerization processes is to convert ethylbenzene to more readily removable species without undue loss of xylenes.

Various methods are known in the art for increasing the para-selectivity of zeolite catalysts. These typically involve modifying the diffusion characteristics of the zeolite so that the rate at which the unwanted reaction products can diffuse into and out of the zeolite pores is reduced as compared to the diffusion rate of the desired para-product. For example, U.S. Pat. No. 4,117,026 describes a selectivation process in which the ortho-xylene sorption rate of the zeolite is increased by depositing a layer of coke on the surface of the zeolite.

It is also known to increase the para-selectivity of a zeolite by depositing on the zeolite an oxide of a metal, such as an alkaline earth metal (U.S. Pat. No. 4,288,647), a Group IIIB metal, for example gallium, indium and/or thallium (U.S. Pat. No. 4,276,437), a Group IVA metal, for example titanium and/or zirconium (U.S. Pat. No. 4,302,620) and a Group IVB metal, for example tin and/or germanium (U.S. Pat. No. 4,278,827).

An alternative selectivation process described in, for example, U.S. Pat. Nos. 5,173,461, 4,950,835, 4,927,979, 4,465,886, 4,477,583, 4,379,761, 4,145,315, 4,127,616, 4,100,215, 4,090,981, 4,060,568 and 3,698,157, is to contact the zeolite with a selectivating agent containing a silicon compound. Such known methods include both ex-situ and in-situ silicon selectivation. In ex-situ selectivation the zeolite is pre-treated with the silicon-containing selectivating agent outside the reactor used for desired shape selective aromatic conversion process. In in-situ selectivation the zeolite is loaded in the aromatic conversion reactor and, during a start-up phase of the reaction, is contacted with a mixture of the silicon-containing selectivating agent and an organic carrier, such as toluene. A combination of both ex-situ and in-situ silicon selectivation can be used. In either event, the selectivation procedure results in the deposition of a silica coating on the surface of the zeolite which modifies the diffusion characteristics of the zeolite.

Traditionally, ex-situ pre-selectivation of zeolites has involved a single application of the selectivating agent. However, U.S. Pat. No. 5,476,823 discloses a process for modifying the shape selectivity of a zeolite by exposing the zeolite to at least two ex-situ selectivation sequences, each of which includes the steps of contacting the zeolite with a silicon-containing selectivating agent in an organic carrier and subsequently calcining the zeolite.

Unexpectedly, it has now been found that certain large crystal forms of ZSM-5, which have a high aluminum content and an unusual aluminum distribution, with the $SiO_2/Al_2O_3$ ratios in bulk being essentially the same as those on the surface, are more responsive to selectivation than conventional ZSM-5 crystals. Such large crystal forms of ZSM-5 are described in International Application No. PCT/US96/09878 which describes a synthetic porous crystalline material having the structure of ZSM-5 and a composition involving the molar relationship $X_2O_3$:$(n)YO_2$, wherein X is a trivalent element, such as aluminum, boron, iron and/or gallium, preferably aluminum; Y is a tetravalent element such as silicon and/or germanium, preferably silicon; and n is greater than about 12, and wherein the crystals have a major dimension of at least about 0.5 micron and a surface $YO_2/X_2O_3$ ratio which is no more than 20% grater than the bulk $YO_2/X_2O_3$ ratio of the crystal.

It is to be appreciated that, although ZSM-5 is normally synthesized as an aluminosilicate, the framework aluminum can be partially or completely replaced by other trivalent elements, such as boron, iron and/or gallium, and the framework silicon can be partially or completely replaced by other tetravalent elements such as germanium.

Accordingly, the invention resides in one aspect in shape-selective catalyst comprising a synthetic porous crystalline material having the structure of ZSM-5 and a composition involving the molar relationship:

$$X_2O_3\text{:}(n)YO_2,$$

wherein X is a trivalent element, such as aluminum, boron, iron and/or gallium, preferably aluminum; Y is a tetravalent element such as silicon and/or germanium, preferably silicon; and n is greater than about 12, and wherein the crystals have a major dimension of at least about 0.5 micron and a surface $YO_2/X_2O_3$ ratio which is no more than 20% less than the bulk $YO_2/X_2O_3$ ratio of the crystal; the catalyst having a diffusion-modifying surface coating of a refractory material.

Preferably, the crystals have a major dimension of at least about 1 micron.

Preferably, the surface $YO_2/X_2O_3$ ratio is no more than 10% less than the bulk $YO_2/X_2O_3$ ratio of the crystal.

Preferably, n is less than about 100 and more preferably is about 25 to about 40.

Preferably, the surface coating is selected from the group consisting of coke, a metal oxide, a non-metal oxide and a non-oxide ceramic and most preferably comprises silica.

In a further aspect, the invention resides in a selective hydrocarbon conversion process using the catalyst of said one aspect of the invention.

The present invention provides a shape-selective catalyst in which a particular form of large crystal ZSM-5 is provided with a diffusion-modifying surface coating of a refractory material so as to enhance its selectivity in hydrocarbon conversion processes, such as toluene disproportionation. As used herein, the term "refractory material" is intended to mean a material which is able to withstand the conditions experienced in a desired hydrocarbon conversion process without significant change in chemical or physical composition.

The particular form of large crystal ZSM-5 used in the catalyst of the invention is described in International Application No. PCT/US96/09878 and has a composition involving the molar relationship:

$$X_2O_3:(n)YO_2,$$

wherein X is a trivalent element, such as aluminum, boron, iron and/or gallium, preferably aluminum; Y is a tetravalent element such as silicon and/or germanium, preferably silicon; and n is greater than about 12, preferably less than 100 and most preferably 25–40, and wherein the crystals have a surface $YO_2/X_2O_3$ ratio which is no more than 20% less, and preferably no more than 10% less, than the bulk $YO_2/X_2O_3$ ratio of the crystal. In contrast, conventional large crystal forms of ZSM-5 are aluminum-rich and have a surface $SiO_2/Al_2O_3$ ratio which is significantly less (>20% less) than the bulk $SiO_2/Al_2O_3$ ratio.

The term "large crystal" ZSM-5 is used herein to mean that the crystals have a major dimension, and preferably at least two dimensions, of at least about 0.5 micron, preferably at least 1 micron and most preferably about 1 to about 10 microns as measured by standard SEM techniques. The crystal size of ZSM-5 can also be deduced from sorption measurements, again by measuring the rate of sorption of 2,2-dimethylbutane at 120° C. and 60 torr (8 kPa) hydrocarbon pressure. The relation between crystal size measured in microns, d, and diffusion time measured in minutes, $t_{0.3}$, the time required for the uptake of 30% capacity of hydrocarbon, is:

$$d=0.704 \times t_{0.3}^{1/2}$$

Prior to application of the diffusion-modifying surface coating, the large crystal ZSM-5 according to the invention preferably has a sorption time, $t_{0.3}$, of at least 5 minutes, preferably at least 10 minutes and more preferably at least 15 minutes.

The novel large crystal ZSM-5 of the invention is produced from a reaction containing sources of an alkali or alkaline-earth metal (M) oxide, a trivalent metal oxide $X_2O_3$, a tetravalent metal oxide $YO_2$, water, and an amino acid or salt thereof (AA) having the formula:

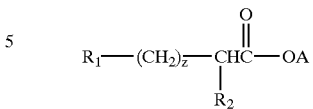

wherein $R_1$ is $NH_2$, $NHR_3$ where $R_3$ is an adamantane or cyclic alkyl group, or is a carboxylic acid group or salt thereof; $R_2$ is H, alkyl, aryl, alkaryl, $NH_2$ or $NHR_3$ where $R_3$ is an adamantane or cyclic alkyl group; A is H or a metal and z is from 0 to 15, preferably 1–7; provided that at least one of $R_1$ and $R_2$ is $NH_2$ or $NHR_3$. Examples of suitable amino acids are 6-aminohexanoic acid, N-2-adamantylglycine, N-cyclohexylglycine, lysine, and glutamic acid (and its monosodium salt). Glutamic acid and its monosodium salt are particularly preferred.

The reaction mixture has a composition, expressed in terms of mole ratios of oxides, as follows:

|  | Useful | Preferred |
|---|---|---|
| $YO_2/X_2O_3$ | 20–80 | 20–40 |
| $H_2O/YO_2$ | 10–90 | 20–60 |
| $AA/YO_2$ | 0.05–0.5 | 0.1–0.2 |
| $M/YO_2$ | 0.1–0.8 | 0.3–0.4 |

The synthesis method of the invention functions with or without added nucleating seeds. In a preferred embodiment, the reaction mixture contains no nucleating seeds. The preferred aluminum source is $NaAlO_2$, while the preferred silicon source is $SiO_2$ sol (30% $SiO_2$ in $H_2O$), which is commercially available as Catalog No. SX0140-1 from EM Science, Inc.

Crystallization is carried out under either stirred or static conditions at a temperature of 80 to 225° C., preferably 120 to 180° C., for 24 hours to 60 days. The resultant ZSM-5 crystals are separated from the mother liquor and recovered and the zeolite is converted to the hydrogen form.

Since the large crystal ZSM-5 used in the catalyst of the invention can be synthesized with a relatively low silica/alumina molar ratio (that is with a relatively high aluminum content), the resultant large crystal ZSM-5 can have a high catalytic activity. Catalytic activity of zeolites, such as ZSM-5, is typically measured by Alpha Value, which compares the catalytic cracking activity of the catalyst (rate of normal hexane conversion per volume of catalyst per unit time) with the activity of a standard silica-alumina cracking catalyst. The Alpha Test is described in U.S. Pat. No. 3,354,078; in the *Journal of Catalysis*, Vol. 4, p. 527 (1965); Vol. 6, p. 278 (1966); and Vol. 61, p. 395 (1980). The experimental conditions of the test used herein include a constant temperature of 538° C. and a variable flow rate as described in detail in the *Journal of Catalysis*, Vol. 61, p. 395. In the hydrogen form and prior to application of the diffusion-modifying surface coating, the large crystal ZSM-5 used in the catalyst of the invention preferably has an Alpha Value in excess of 300 and preferably in excess of 800.

Surprisingly, it is found that this novel form of ZSM-5 is unusually responsive to selectivation by the application of a diffusion-modifying surface coating of a refractory material. This responsiveness may take the form of more rapid surface modification or improved catalyst properties or both. The refractory coating is conveniently coke or an oxide of a metal or a non-metal, such as silicon, boron and/or titanium. Alternatively, the refractory coating could comprise an non-oxide ceramic, such as boron nitride.

In one preferred embodiment, the diffusion-modifying surface coating is silica and is applied as an organosilicon compound by ex-situ pre-selectivation and/or by in-situ selectivation.

A suitable ex-situ pre-selectivation process is described in U.S. Pat. No. 5,476,823 and involves contacting the zeolite with the organosilicon compound in an organic carrier, calcining the zeolite and then repeating the contacting and calcining sequence one or more times. Using the large crystal zeolite of the invention, the number of sequences necessary to achieve a given para-selectivity is reduced as compared with conventional forms of ZSM-5. An alternative ex-situ selectivation procedure which can be used in place of, or more preferably, in addition to that disclosed in U.S. Pat. No. 5,476,823 is described in U.S. Pat. No. 5,365,003 and involves agglomerating a mixture of the zeolite, an organosilicon compound and optionally a binder in a muller and then calcining the resultant agglomerates.

A suitable in-situ selectivation procedure is described in U.S. Pat. No. 5,498,814 and involves contacting the zeolite with a mixture of toluene, hydrogen and an organosilicon compound at a temperature of 350–540° C., a pressure of atmospheric-5000 psig (100–35000 kPa) and a hydrogen to hydrocarbon mole ratio of 0.1–20 until the desired para-selectivity is reached. Again, using the large crystal zeolite of the invention, the time required to achieve a given para-selectivity is reduced as compared with conventional forms of ZSM-5.

Useful silicon selectivating agents include silicones and siloxanes which can be characterized by the general formula:

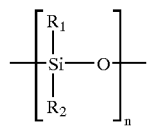

where $R_1$ is hydrogen, halogen, hydroxyl, alkyl, halogenated alkyl, aryl, halogenated aryl, aralkyl, halogenated aralkyl, alkaryl or halogenated alkaryl. The hydrocarbon substituents generally contain from 1 to 10 carbon atoms, preferably methyl or ethyl groups. $R_2$ is independently selected from the same group as $R_1$, and n is an integer of at least 2 and generally in the range of 3 to 1000. The molecular weight of the silicone compound employed is generally between about 80 and about 20,000 and preferably within the approximate range of 150 to 10,000. Representative silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone and ethylvinyl silicone. The silicone compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used, as may silicones with other functional groups.

Other silicon compounds, including silanes and alkoxy silanes, such as tetramethoxy silane, may also be utilized. These useful silicon-containing selectivating agents include silanes characterizable by the general formula:

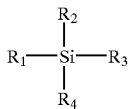

where $R_1$, $R_2$, $R_3$ and $R_4$ are independently selected from the group consisting of hydrogen, hydroxyl, halogen, alkyl, halogenated alkyl, alkoxy, aryl, halogenated aryl, aralkyl, halogenated aralkyl, alkaryl, and halogenated alkaryl groups. Mixtures of these compounds may also be used.

Preferred silicon-containing selectivating agents include dimethylphenylmethyl polysiloxane (e.g., Dow-550) and phenylmethyl polysiloxane (e.g., Dow-710). Dow-550 and Dow-710 are available from Dow Chemical Co.

Preferably, the kinetic diameter of the silicon-containing selectivating agent is larger than the zeolite pore diameter, in order to avoid entry of the selectivating agent into the pore and any concomitant reduction in the internal activity of the catalyst.

After the or each application of the silicon-containing selectivating agent, the zeolite is calcined at 350–550° C. for 1–24 hours to convert the orgaonosilicon compound to silica.

In an alternative embodiment, the diffusion-modifying surface coating comprises coke and is produced by ex-situ or in-situ precoking of the zeolite. Precoking is conveniently effected by passing an aromatic hydrocarbon, such as toluene, over the zeolite at a relatively high temperature of 500–650° C. so as to deposit at least about 1 wt %, preferably 1–30 wt %, coke thereon.

The catalyst of the invention may include a binder or matrix material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material which is active tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the ZSM-5 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided ZSM-5 material and inorganic oxide matrix vary widely, with the ZSM-5 content ranging from about 1 to about 90% by weight and more usually in the range of about 2 to about 80 wt. % of the composite.

It is to be appreciated that, although the binder or matrix and the diffusion modifying refractory coating can be formed of the same material, such as silica, these are separate components of the catalyst normally formed by different steps in the catalyst production process. For example, the ZSM-5 may be composited with the binder or matrix and the resultant composite provided with a coating of a refractory material. Alternatively, the refractory coating may be applied to the ZSM-5 crystals before the latter are composited with the binder or matrix.

A hydrogenation/dehydrogenation function may be introduced into the catalyst of the invention, such as by addition of a metal compound such as platinum. While platinum is the preferred metal, other metals of Groups IB to VIII of the Periodic Table such as palladium, nickel, copper, cobalt, molybdenum, rhodium, ruthenium, silver, gold, mercury, osmium, iron, zinc, cadmium, and mixtures thereof, may be utilized. The metal may be added by cation exchange, in amounts of from about 0.001% to about 2%, typically about 0.5%. For example, a platinum modified catalyst can be prepared by contacting the catalyst with an aqueous solution of tetraammine platinum(II) nitrate or tetraammine platinum (II) chloride. The catalyst can then be filtered, washed with water and calcined at temperatures of from about 250 to about 500° C.

The catalyst of the invention is useful in a wide variety of shape selective hydrocarbon conversion processes including, as non-limiting examples, selective hydrocarbon cracking, for example of n-paraffins to reduce pour point, of hydrocarbons with reaction conditions including a temperature of from about 300° C. to about 700° C., a pressure of from about 0.1 atmosphere (bar) to about 30 atmospheres (10 to 3000 kPa) and a weight hourly space velocity of from about 0.1 $hr^{-1}$ to about 20 $hr^{-1}$; converting paraffins or olefins to aromatics, e.g. benzene, toluene and xylene, with reaction conditions including a temperature of from about 100° C. to about 700° C., a pressure of from about 0.1 atmosphere to about 60 atmospheres (10 to 6000 kPa), a weight hourly space velocity of from about 0.5 to about 400 and a hydrogen/hydrocarbon mole ratio of from about 0 to about 20; isomerizing alkylaromatics, such as xylenes, to a product rich in the para-isomer with reaction conditions including a temperature of from about 250° C. to about 540° C., a pressure of from about 0 to about 1000 psig (100 to 7000 kPa), a weight hourly space velocity of from about 0.1 to about 250 and a hydrogen/hydrocarbon mole ratio of from about 0 to about 20; disproportionating alkyl aromatics, such as toluene and ethylbenzene, with reaction conditions including a temperature of from about 100° C. to about 600° C., a pressure from about 0 to about 2000 psig (100 to 14000 kPa), a hydrogen/hydrocarbon mole ratio of from about 0 to about 10 and a weight hourly space velocity of from about 0.1 to about 100; alkylating aromatic hydrocarbons, e.g. benzene and alkylbenzenes in the presence of an alkylating agent, e.g. olefins, formaldehyde, alkyl halides and alcohols, with reaction conditions including a temperature of from about 250° C. to about 500° C., a pressure of from about atmospheric to about 200 atmospheres (100 to 20000 kPa), a weight hourly space velocity of from about 2 to about 2000 and an aromatic hydrocarbon/alkylating agent mole ratio of from about 1/1 to about 20/1; and dealkylating alkylaromatics, such conversion of ethylbenzene to benzene and $C_2$-light gas, with reaction conditions including a temperature of from about 200° C. to about 540° C., a pressure of from about 0 to about 1000 kPa (100 to 7000 kPa), a weight hourly space velocity of from about 0.1 to about 200 and a hydrogen/hydrocarbon mole ratio of from about 0.5 to about 20.

In one preferred embodiment, where the catalyst of the invention is used in toluene disproportionation, conditions for the process preferably include a temperature of 350–540° C., a pressure of 15–800 psig (200–5600 kPa), a mole ratio of hydrogen to hydrocarbon of 0.1–10, and a WHSV of 1–10.

In another preferred embodiment, where the catalyst of the invention is used in xylene isomerization, conditions for the process preferably include a temperature of 350–500° C., a pressure of 50–400 psig (400–3000 kPa), a mole ratio of hydrogen to hydrocarbon of 1–10, and a WHSV of 3–50.

In order to more fully illustrate the nature of the invention and the manner of practicing same, the following examples are presented. In the Examples, references are made to the characteristic diffusion rates of particular porous crystalline materials for 2,2-dimethylbutane. The characteristic diffusion rate is defined as $D/r^2 \times 10^6$, wherein D is the diffusion coefficient ($cm^2$/sec) and r is the crystal radius (cm). The required diffusion parameters can be derived from sorption measurements provided the assumption is made that the plane sheet model describes the diffusion process. Thus for a given sorbate loading Q, the value $Q/Q_4$, where $Q_4$ is the equilibrium sorbate loading and is directly proportional to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967. The characteristic diffusion rate is measured at a temperature of 120° C. and a 2,2-dimethylbutane pressure of 60 torr (8 kPa)

EXAMPLE 1

1.0 part of $Al_2(SO_4)_3 \cdot xH_2O$ was dissolved in 8.0 parts of $H_2O$. To this solution was added 1.98 parts of 50% sodium hydroxide solution. A solution obtained by dissolving 1.12 parts of the mono sodium salt of glutamic acid (MSG) in 2.71 parts of $H_2O$ was added to the above solution. To this mixture was added 4.03 parts of Ultrasil precipitated silica. The slurry was thoroughly mixed and then 0.1 part of ZSM-5 seeds (solids basis) slurried in 2.28 parts of $H_2O$ was added to the mixture and the final slurry mixed for 30 minutes. The composition of the reaction mixture in mole ratios was:

$SiO_2/Al_2O_3$=36.0

$OH/SiO_2$=0.24

$Na+/SiO_2$=0.50

$R/SiO_2$=0.10

$H_2O/SiO_2$=12.8

The mixture was crystallized in a stainless steel reactor, with stirring, at 100 rpm, at 156° C. for 60 hrs. The crystalline product was isolated by filtration and calcined for 16 hrs. at 538° C. X-ray analysis of the product showed a crystalline ZSM-5 material. The bulk silica/alumina molar ratio of the material was 29.6.

EXAMPLE 2

The calcined product from Example 1 was contacted with 10% $NH_4Cl$ solution for three 1 hr contacts at 85° C., with stirring. The material was then calcined for 3 hrs. at 538° C. to convert it to the hydrogen form. The material was found to have an alpha value of 1454. Scanning Electron Microscopy (SEM) showed the presence of 1–3 micron crystals.

EXAMPLE 3

A sample of the calcined product from Example 1 was mixed with Ultrasil VN3SP silica and Ludox HS-40 silica to give a mixture composed of 65% ZSM-5/17.5% $SiO_2$ from Ultrasil/17.5% $SiO_2$ from Ludox on a 100% solids basis. Deionized (DI) water and 3% NaOH (on 100% solids basis) was added to give an extrudable mix which was extruded to 1/16 inch (1.6 mm) diameter. The extrudate was dried at 120° C., exchanged with 1N $NH_4NO_3$ solution, washed with DI water, dried again at 120° C. and calcined at 540° C. for 3 hours. The ammonium exchange, washing, drying and calcination was repeated to give a catalyst with an alpha value of 1017 and a sodium content of 70 ppm. The catalyst, identified herein as Catalyst A, exhibited a characteristic diffusion rate for 2,2-dimethylbutane of 27 $sec^{-1}$ as measured at 120° C. and 60 torr (8 kPa) hydrocarbon pressure.

EXAMPLE 4

Catalyst A from Example 3 was ex-situ silicon selectivated by impregnation at room temperature with Dow 550 in n-decane such that the components were in the weight ratio 1 part catalyst: 1.1 part n-decane: 0.08 part Dow 550. After impregnation, the solvent was stripped by evaporation and the catalyst calcined at 540° C. firstly in nitrogen for 2 hours and then in air for 6 hours to give Catalyst B. The same selectivation procedure was repeated for second and third cycles to give Catalysts C and D respectively, with small samples being removed after each cycle for catalytic evaluation.

The characteristic diffusion rates for 2,2-dimethylbutane as measured at 120° C. and 60 torr (8 kPa) hydrocarbon pressure for the selectivated catalysts were as follows:

Catalyst B (1×selectivation)–7.5 $sec^{-1}$

Catalyst C (2×selectivation)–2.3 $sec^{-1}$

Catalyst D (3×selectivation)–1.6 $sec^{-1}$

Catalytic evaluation of each selectivated sample was effected by mixing 2 gram of the sample with inert sand and loading the mixture into a 0.375 inch (9.5 mm) diameter tube reactor. The reactor was heated in hydrogen and a 2:1 hydrogen/toluene feed was introduced at 3 WHSV, 270 psig (1960 kPa). The temperature was adjusted to achieve a toluene conversion of about 30% by weight and the p-xylene selectivity (by weight of the $C_8$ product) was measured. The results are given in Table 1 below.

By way of comparison, a series of four prior art catalysts were produced from ZSM-5 having a crystal size less than 0.5. The catalysts were subjected to one (Catalyst E), two (Catalyst F), three (Catalyst G), and four (Catalyst H) of the selectivation cycles described above and and were tested in the same manner as the Catalysts B–D of the invention. The results are also given in Table 1.

TABLE 1

| Catalyst | | No. of Selectivations | Temperature, ° C. | % Toluene Conversion | P-xylene Selectivity |
|---|---|---|---|---|---|
| Invention | B | 1 | 390 | 30 | 37.4 |
| | C | 2 | 395 | 30 | 79.4 |
| | D | 3 | 395 | 30 | 89.3 |
| Prior art | E | 1 | 395 | 30 | 24.9 |
| | F | 2 | 410 | 30 | 30.9 |
| | G | 3 | 416 | 30 | 63.0 |
| | H | 4 | 428 | 30 | 86.4 |

From Table 1 it will be seen that the catalyst using the large crystal ZSM-5 of the invention reached a toluene conversion of 30% and a p-xylene selectivity of about 90% at a temperature of 395° C. after only 3 ex-situ silicon-selectivation steps (Catalyst D). In contrast, the catalysts using the prior art ZSM-5 required 4 selectivation steps and a temperature of 428° C. to reach the same toluene conversion and p-xylene selectivity levels (Catalyst H).

EXAMPLE 5

A sample of the calcined ZSM-5 product from Example 1 was mixed with Ultrasil VN3SP silica and mulled for 5 minutes. To this mix was added 14% by weight of solids of Dow 550 resin (a polysiloxane) dissolved in 23% of dibasic ester, followed by Ludox HS-40 silica, then 50% NaOH (to give 3% NaOH on 100% solids basis) dissolved in enough water to give an extrudable mull. The proportions of ZSM-5, Ultrasil and Ludox used were such as to give 65% ZSM-5/ 17.5% $SiO_2$ ex Ultrasil/17.5% $SiO_2$ ex Ludox on 100% solids basis. The resultant mix was extruded to 1/16 inch (1.6 mm) diameter. The extrudates were dried at 120° C. and subjected to 4 cycles of the ammonium exchange/calcination sequence described in Example 3 to give a catalyst with an alpha value of 1089, a sodium content of 2200 ppm and a characteristic diffusion rate for 2,2-dimethylbutane of 4.3 $sec^{-1}$ as measured at 120EC and 60 torr (8 kPa) hydrocarbon pressure. The resultant catalyst, identified as Catalyst I, was subjected to catalytic testing as in Example 4 and the results are given in Table 2.

EXAMPLE 6

A sample of Catalyst I from Example 5 was ammonium exchanged/calcined to reduce its sodium level to less than 700 ppm and was then subjected to a single ex-situ silicon-selectivation procedure as described in Example 4. The resultant catalyst, identified as Catalyst J, and samples of Catalyst A (example 3) and Catalyst F (prior art catalyst of Example 4) were subjected to catalytic testing as in Example 4. The results are listed in Table 2.

TABLE 2

| Catalyst | A | I | J | F |
|---|---|---|---|---|
| No. of ex-situ selectivations | 0 | 0 | 1 | 2 |
| Temp. ° C. | 400 | 410 | 401 | 396 |
| Pressure (psig) | 272 | 272 | 275 | 275 |
| $H_2$:HC | 2 | 2 | 2 | 2 |
| Toluene Conv., wt % | 30 | 29.9 | 29.3 | 30.4 |
| Xylene Yield, wt. % | 16.1 | 16.1 | 14.3 | 15.8 |
| p-Xylene Selectivity, wt % | 24 | 31.9 | 86.0 | 51.9 |

TABLE 2-continued

| Catalyst | A | I | J | F |
|---|---|---|---|---|
| Ethylbenzene Selectivity, wt % | 1.0 | 1.0 | 2.4 | 1.56 |
| Benzene/Xylene (molar) | 1.1 | 1.1 | 1.25 | 1.11 |
| $C_5^-$ | 0.5 | 0.4 | 0.89 | 0.58 |
| $C_9^+$ | 0.6 | 0.7 | 0.72 | 0.79 |

It will be seen from Table 2 that co-extrusion of the ZSM-5 of Example 1 with the Dow 550 organosilicon compound resulted in a base catalyst, Catalyst I, which was more selective for p-xylene production than the base catalyst coextruded with silica, Catalyst A. In addition, a single selectivation cycle of the base catalyst co-extruded with Dow 550 resulted in an increase of p-xylene selectivity to 86% (Catalyst J), compared with a p-xylene selectivity of only 37.4% after the first selectivation cycle for the catalyst coextruded with silica (see Catalyst B in Table 1).

In contrast, where the catalyst was produced from ZSM-5 with a crystal size of 0.2–0.5 micron, 2 ex-situ selectivation cycles resulted in a p-selectivity of only 52% (Catalyst F in Table 2).

EXAMPLE 7

A sample of the calcined ZSM-5 product from Example 1 was mixed 20 with LaRoche Versal 300 alumina in proportion to give 65:35 ZSM-5:$Al_2O_3$ on a 100% solids basis, and mulled for 10–15 minutes. Sufficient DI water was then added over a 10-minute period to give an extrudable mull. The resultant mix was extruded to 1/16 inch (1.6 mm) diameter. The extrudate was dried at 120° C. and calcined in flowing nitrogen at 540° C. for 3 hours. The calcined exrudate was then exchanged with 1N $NH_4NO_3$ solution, washed with DI water, dried at 120° C. and calcined in flowing air at 540° C. for 3 hours to give a catalyst with an alpha value of 661, a sodium content of <50 ppm and a characteristic diffusion rate for 2,2-dimethylbutane of 110 $sec^{-1}$ as measured at 120° C. and 60 torr (8 kPa) hydrocarbon pressure.

EXAMPLE 8

The catalyst from Example 7 was coke selectivated using a simulated commercial coke-selectivation procedure. 4.0 gms of the catalyst was mixed with inert sand and loaded into a 0.375" (9.5 mm) diameter stainless steel tube reactor. The sample was dried in hydrogen overnight at 300° C. and 235 psig (1720 kPa), whereafter the catalyst bed temperature was increased to 565° C. and toluene (1.67 $hr^{-1}$), $H_2$ (0.5 $H_2$:HC) and $N_2$ (1.5 $N_2$:HC) flows were established to start the coking procedure. After 1.3 days on stream, the coking procedure was stopped and the catalyst was hydrogen stripped at 470° C. overnight to remove any reactive species from the catalyst. Following hydrogen stripping, the reactor pressure was increased to 270 psig (1960 kPa), the reactor temperature adjusted to 400° C. and toluene and hydrogen flows were established to the reactor at 3 $hr^{-1}$ WHSV and 1 $H_2$/HC. The reactor effluent was continuously monitored and the temperature adjusted to achieve approximately 30% toluene conversion. A summary of the catalytic data is shown in Table 3.

TABLE 3

| Coking Time, days | 1.30 |
|---|---|
| WHSV, hr–1 | 3 |
| H2:HC | 1 |
| Temp. ° C. | 385 |
| Press. (psig) | 281 |
| Toluene Conv., wt % | 29.9 |
| Xylene Yield, wt % | 15.6 |
| p-Xylene Sel. wt % | 68.8 |
| Ethylbenzene Sel., wt % | 1.80 |
| Benzene/Xylene (molar) | 1.10 |
| C5– | 0.46 |
| C9+ | 0.94 |

EXAMPLE 9

The previously coke-selectivated catalyst from Example 8 was further coke selectivated at 565° C. for an additional 0.42 days. Hence, at the end of the coking period in this example, the parent catalyst of Example 8 was coke selectivation for a total of 1.72 days. Following the coking and hydrogen stripping procedures outlined in Example 8, the reactor pressure was increased to 270 psig and the reactor temperature adjusted to 400° C. in preparation for catalytic evaluation. Following the second coke-selectivation treatment, toluene and hydrogen flows were established to the reactor at 3 $hr^{-1}$ WHSV, 270 psig and 1 $H_2$/HC. As before, the reactor effluent was continuously monitored and the reactor temperature adjusted to achieve about 30% toluene conversion. A summary of the catalytic data is shown in Table 4.

TABLE 4

| Coking Time, days | 1.72 |
|---|---|
| WHSV, $hr^{-1}$ | 3 |
| $H_2$:HC | 1 |
| Temp. ° C. | 396 |
| Press. (psig) | 276 |
| Toluene Conv., wt % | 29.0 |
| Xylene Yield, wt % | 14.8 |
| p-Xylene Sel. wt % | 83.3 |
| Ethylbenzene Sel., wt % | 2.21 |
| Benzene/Xylene (molar) | 1.13 |
| $C_5^-$ | 0.61 |
| $C_9^+$ | 0.91 |

EXAMPLE 10

The previously coke-selectivated catalyst from Example 9 was further coke-selectivated at 565° C. for an additional 0.47 days. Hence, at the end of the coking period in this example the parent catalyst of Example 7 was coke-selectivated for a total of 2.19 days. Following the coking and hydrogen stripping procedures outlined in Example 8, the reactor pressure was increased to 270 psig and the reactor temperature adjusted to 400° C. in preparation for catalytic evaluation. Following the third coke-selectivation treatment, toluene and hydrogen flows were established to the reactor at 3 $hr^{-1}$ WHSV, 270 psig and 1.5–2 $H_2$/HC. As before, the reactor effluent was continuously monitored and the reactor temperature adjusted to achieve about 30% toluene conversion. A summary of the catalytic data is shown in Table 5.

TABLE 5

| Coking Time, days | 2.19 | 2.19 |
|---|---|---|
| WHSV, hr$^{-1}$ | 3 | 3 |
| H$_2$:HC | 2 | 1.5 |
| Temp. ° C. | 416 | 415 |
| Press. (psig) | 271 | 276 |
| Toluene Conv., wt % | 30.6 | 30.0 |
| Xylene Yield, wt % | 12.7 | 12.8 |
| p-Xylene Sel. wt % | 92.7 | 92.5 |
| Ethylbenzene Sel., wt % | 3.50 | 3.31 |
| Benzene/Xylene (molar) | 1.58 | 1.50 |
| C$_5^-$ | 1.80 | 1.55 |
| C$_9^+$ | 0.97 | 0.94 |

Following the third coking treatment, the catalyst was highly selective for p-xylene formation, giving nearly 93% p-xylene selectivity at 416° C. and 30% toluene conversion, albeit at slightly reduced xylene yield as compared with the catalyst of Example 9.

What is claimed is:

1. A shape-selective catalyst comprising a synthetic porous crystalline material having the structure of ZSM-5 and a composition involving the molar relationship:

$$X_2O_3:(n)YO_2,$$

wherein X is a trivalent element, selected from the group consisting of aluminum, boron, iron and gallium; Y is a tetravalent element selected from the group consisting of silicon and germanium; and n is greater than about 12, and wherein the crystals have a major dimension of at least about 0.5 micron and a surface YO$_2$/X$_2$O$_3$ ratio which is no more than 20% less than the bulk YO$_2$/X$_2$O$_3$ ratio of the crystal; the catalyst having a diffusion-modifying surface coating of a refractory material.

2. The catalyst of claim 1 wherein X is selected from the group consisting of aluminum, boron, iron and gallium, and Y is selected from the group consisting of silicon and germanium.

3. The catalyst of claim 1 wherein X is aluminum and Y is silicon.

4. The catalyst of claim 1 wherein n is less than about 100.

5. The catalyst of claim 1 wherein n is about 25 to about 40.

6. The catalyst of claim 1 wherein the crystals have a major dimension of at least about 1 micron.

7. The catalyst of claim 1 wherein the diffusion-modifying surface coating is selected from the group consisting of coke, a metal oxide, a non-metal oxide and a non-oxide ceramic.

8. The catalyst of claim 1 wherein the diffusion-modifying surface coating comprises silica.

9. The catalyst of claim 8 wherein the silica coating is produced by the steps of (a) treating the zeolite with an organosilicon compound and (b) converting the organosilicon compound to silica.

10. The catalyst of claim 9 wherein step (a) is effected during mixing of the zeolite with particles of a binder or matrix.

11. The catalyst of claim 9 wherein steps (a) and (b) are repeated at least once.

12. The catalyst of claim 1 wherein the diffusion-modifying surface coating comprises coke.

13. A process for shape selective hydrocarbon conversion comprising contacting a reaction stream comprising a hydrocarbon to be converted, under conversion conditions, with the catalyst of claim 1.

14. The process of claim 13 wherein the shape selective hydrocarbon conversion is selected from a group consisting of selective hydrocarbon cracking, isomerization of alkylaromatics, disproportionation of alkylaromatics, alkylation of aromatics, dealkylation of alkylaromatics and conversion of paraffins and olefins to aromatics.

15. The process of claim 14 wherein the feedstream comprises toluene and the conversion is the selective disproportionation of toluene to para-xylene.

16. The process of claim 15 wherein the conversion is effected at a temperature of from about 100° C. to about 600° C., a pressure from about 0 to about 2000 psig (100 to 14000 kPa), a hydrogen/hydrocarbon mole ratio of from about 0 to about 10 and a weight hourly space velocity of from about 0.1 to about 100.

17. The process of claim 15 wherein the conversion is effected at a temperature of 350–540° C., a pressure of 15–800 psig (200-5600 kPa), a mole ratio of hydrogen to hydrocarbon of 0.1–10, and a weight hourly space velocity of about 1–10.

* * * * *